United States Patent [19]
Uffenheimer

[11] 3,954,341
[45] May 4, 1976

[54] LIQUID SAMPLE ANALYZER WITH IMPROVED OPTICAL CHARACTERISTICS

[75] Inventor: Kenneth F. Uffenheimer, Yonkers, N.Y.

[73] Assignee: Technicon Instruments Corporation, Tarrytown, N.Y.

[22] Filed: Sept. 30, 1974

[21] Appl. No.: 510,829

[52] U.S. Cl. .............................. 356/181; 250/576; 356/246
[51] Int. Cl.² ........................................ G01N 1/10
[58] Field of Search ............ 250/576; 356/181, 244, 356/246, 75; 350/96 LM

[56] References Cited
UNITED STATES PATENTS 3,236,602  2/1966  Isreeli .......................... 356/246 X
3,770,350  11/1973  Stone et al. ........................ 356/75

Primary Examiner—John K. Corbin
Assistant Examiner—F. L. Evans
Attorney, Agent, or Firm—S. P. Tedesco; S. E. Rockwell

[57] ABSTRACT

A quantitative liquid sample analysis system exhibiting improved light transmission along the sight path of a flowcell and greater optical stability for significantly more accuracy of analytical results. There is provided in such a system a source of treated liquid having a first index of refraction, means for flowing the liquid along a conduit, the conduit including a flowcell having a tubular wall structure with a second index of refraction, the second index of refraction being less than the first index of refraction.

7 Claims, 3 Drawing Figures

LIQUID SAMPLE ANALYZER WITH IMPROVED OPTICAL CHARACTERISTICS

BACKGROUND OF THE INVENTION

1. Field of the Invention

This invention relates to a liquid analysis system having improved optical characteristics.

2. Prior Art

The invention is concerned with automated quantitative analysis of the continuous flow type, and especially the optical characteristics of such analysis utilizing a colorimeter, densitometer or fluorometer. Skeggs et al U.S. Pat. No. 3,241,432; Rosin et al U.S. Pat. No. 3,345,910; Rachlis et al U.S. Pat. No. 3,583,817; and Bellinger et al U.S. Pat. No. 3,740,158 disclose method and apparatus which exemplify the prior art.

The Skeggs et al U.S. Pat. No. 3,241,432 describes automated quantitative analysis of a series of liquid samples seriatum, wherein neighboring samples flowing along a conduit are separated by an immiscible fluid segment which is preferably a gas segment. The samples are treated and after removal of the immiscible fluid segments are flowed through a colorimeter flowcell (FIG. 7), having a straight sight path extending through curved surfaces of the glass cell, for photometric analysis. However, the curved glass surfaces, end window, through which light is directed, while having good fluid flow characteristics for the sweeping away of any fine bubbles or debris, often failed to exhibit optimum optic qualities. For example, some light from the source thereof may be absorbed in the end walls or refracted therefrom, resulting in loss of light transmission.

The Rosin et al U.S. Pat. No. 3,345,910 discloses a flowcell having flat end windows in the sight path, tending to lessen the aforementioned refraction problem of the curved glass end windows of the Skeggs et al flowcell. However, this window configuration caused fluid and debris entrapment in proximity to the lower internal corners of such windows which, when caused to shift somewhat by pulsations in flow in the cell, resulted in optical noise as pointed out in the Rachlis et al U.S. Pat. No. 3,583,817. The last-mentioned patent discloses a flowcell end window which has a planar, internally inclined surface which avoided such entrapment in the cell. However, all of the above-discussed flowcells exhibited loss of light transmission along the sight path caused by refraction of light within the end windows into the tubular wall structure of the flowcell.

The Bellinger et al flowcell of U.S. Pat. No. 3,740,158 alleviated the last-mentioned optical problem. It discloses an interface of a flowcell end window and the tubular wall structure of the cell wherein the material of the window has a higher refractive index than the material of the wall structure, so that the end window constitutes a light pipe for increased light transmission into the liquid in the flowcell path or out of it, or both. In accordance with the Bellinger et al disclosure any immiscible fluid segments in the sample stream may be removed from the stream in the use of the flowcell just prior to introduction of the sample stream into the flowcell. However, it was pointed out that it is preferred that for the purpose of cleansing the cell, these immiscible fluid segments pass through the cell.

In the use of all the above-described flowcells, there has been a loss of transmission of light along the sight path within the cell and in which liquid is conveyed because the liquid failed to exhibit light-piping characteristics therein, that is, light reflectivity within the liquid or, more precisely, reflectivity within the liquid at the interface thereof with the tubular wall structure of the flowcell. The present invention deals with overcoming this problem.

SUMMARY OF THE INVENTION

One object of the invention is to provide improved light transmission through a flowcell, without the substantial high dependence of the past on the configuration and light transmission characteristics of the flowcell end windows, even where the fluid-conveying sight path may have a relatively very small cross sectional dimension on the order of 0.02 inch for example, and where the light source is of relatively low intensity, so that the cell has a high signal-to-noise ratio.

Another object is to provide an improved liquid sample analysis system utilizing a flowcell wherein light transmission through the flowcell is improved by achieving light piping of the liquid within the flowcell sight path. A further object is to provide improved reflectivity at the interface of the liquid in the flowcell sight path with the tubular wall structure of the cell and thereby eliminating or substantially reducing refraction of light into such wall structure. This results in significantly less susceptibility to changes in light transmission through the flowcell caused by small changes in refractive index of the fluid stream.

Still another object is to provide in such liquid sample analysis system such light piping utilizing a flowcell which enables new and diverse flowcell configurations and dimensions, especially length for example, which may be fitted into a small space. There is provided in such a system a source of treated liquid having a first index of refraction, means for flowing the liquid along a conduit, the conduit including a flowcell having a tubular wall structure with a second index of refraction, the second index of refraction being less than the first index of refraction.

DETAILED DESCRIPTION OF THE PREFERRED EMBODIMENTS

Figure 1:
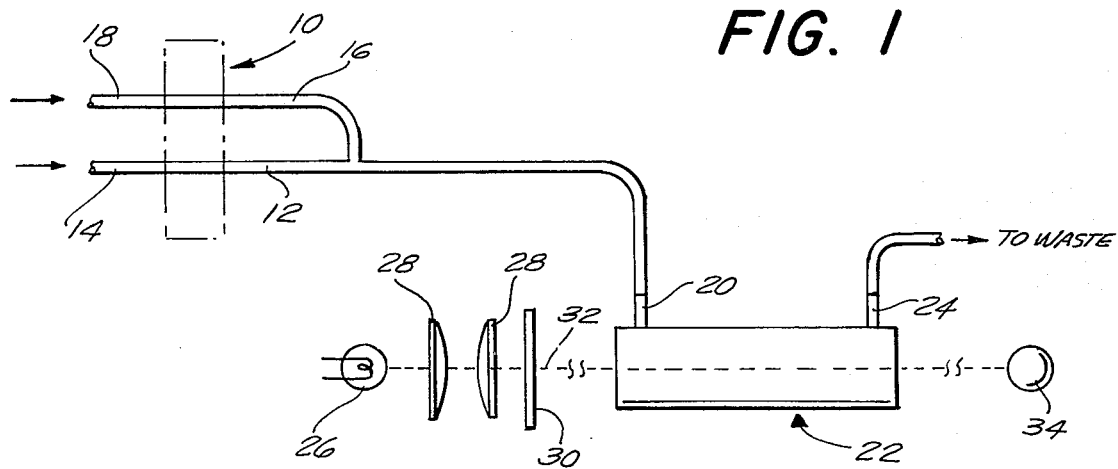
FIG. 1 is a fragmentary diagrammatic view illustrating an automated liquid sample analyzer embodying the invention.
Figure 2:
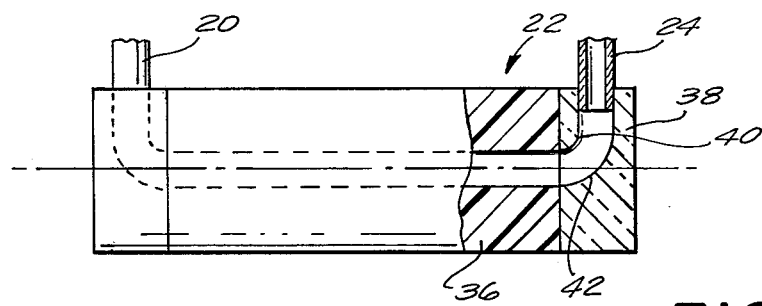
FIG. 2 is an enlarged fragmentary view of the flowcell of FIG. 1 illustrating the same partially broken away.

In the form of FIG. 1, a pump, which may be of the peristalic type, is indicated generally at 10 and has a compressible pump tube 12 extending therethrough for fluid flow in the direction of the arrow. The tube 12 has an inlet portion 14. A compressible pump tube 16 also extends through the pump 10 as indicated and has an inlet portion 18. The outlet end of the tube 16 is coupled to the tube 12 intermediate the ends of the latter, down stream from the pump, for delivery of fluid in the tube 16 into the fluid flowing in the tube 12. A non-illustrated mixing coil may be interposed in the tube 12 intermediate the outlet end of such tube and the junction of the tube 16 to the tube 12 for mixing of the fluids. The outlet end of the tube 12 is coupled to the inlet nipple 20 of a flowcell, indicated generally at 22, which is best shown in FIG. 2. The fluid flowing into and through the sight path of flowcell 22 is outletted from the flowcell through outlet nipple 24 coupled to the inlet of tube 26 conveying the fluid to waste.

A light source includes a lamp 26, and may also include suitable focusing lenses 28. The light source includes a filter 30 of appropriate wave length. A beam of light from the lamp 26 having an optical axis 32 is directed into the sight path of the flowcell 22 for impingement on a photocell 34 as will be explained more fully hereinafter with reference to FIG. 2. The flowcell 22 may be incorporated in a colorimeter or, if desired, may be utilized in a densitometer or a fluorometer.

The inlet portion 14 of the tube 12 may be supplied with an appropriate reagent from a non-illustrated source. The inlet portion 18 of the tube 16 may be supplied from a non-illustrated source of a liquid sample such as a monitoring stream or may be supplied sequentially with a series of liquid samples as described in U.S. Pat. No. 3,134,263 issued to de Jong. That patent describes a sampler for supplying a stream of such samples along a conduit wherein neighboring samples are separated by at least a pair of immiscible fluid segments such as gas and a segment of wash solution between the segments of such pair of immiscible fluid segments. If desired, any immiscible fluid segments may be removed from the fluid stream in tube 12 by non-illustrated conventional venting means just prior to entry of the stream into the flowcell 22. However, it is preferred that any such immiscible fluid segments be passed through the flowcell 22 for their cleansing effect on the internal surfaces of the liquid passageway therethrough. Smythe et al U.S. Pat. No. 3,826,615 describes a sample stream segmentation pattern similar to that of de Jong and having in addition immiscible fluid segments within and separating portions of a single sample. Certain of these immiscible fluid segments within each sample are spaced differently with reference to their neighboring immiscible fluid segments than other immiscible fluid segments. Further, as shown in FIG. 5, a pair of immiscible fluid segments, which may be gas, and each designated A bracket a trailing portion of the first sample S1, the wash solution W and the leading portion of the second sample S2.

As indicated in FIG. 2, the flowcell 22 has a central tubular wall structure 36 which may be structured of Teflon of the type FEP having the nonproprietary designation of fluoronated ethylene-propylene resin having an index of refraction of approximately 1.338. The internal diameter of the cylindrical axial bore or opening defined by the tubular wall structure 36 may be 0.5mm, while the outer diameter may be 5.0mm, by way of sample and not by way of limitation. End caps 38 of glass, for example, are secured as by an etchbond, for example, to the respective ends of the tubular wall structure 36.

As shown in the last-mentioned view each end cap 38 has a bore extending through the top thereof and out the side of the cap nearest the tubular wall structure 36 in alignment with the aforementioned opening defined by the wall structure 36 and of the same internal diameter. The other side of the cap is flat and is polished in the form shown, and forms an end window of the flowcell. The aforementioned bore 40 is formed in part on a radius, as at 42, to facilitate fluid flow through the flowcell for the sweeping away of any fluid or debris in the flowcell. The bore 40 may be formed in accordance with conventional glass-working techniques. The aforementioned nipples 20, 24, which may be of a conventional material, each have the lower end thereof conventionally sealed in the upper end portion of the corresponding bore 40. It will be understood from the foregoing that the nipple 20, the corresponding bore 40, the opening defined by the tubular wall structure 36, the corresponding bore 40 and the nipple 24 together form a fluid passageway through the flowcell. It will be further understood, that the last-mentioned opening defined by the tubular wall structure 36 and indicated at 44 defines a sight path (12mm long for example) of the flowcell together with portions of the respective bores 40 in the end caps along the optical axis 32. Each bore 40 is cylindrical.

Figure 3:
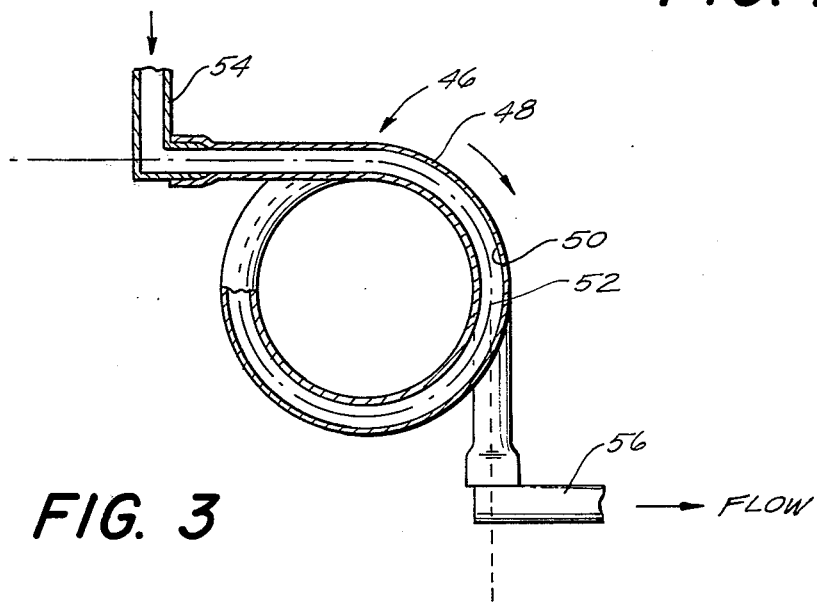
FIG. 3 is a view similar to FIG. 2 illustrating a modified form of the flowcell.

In the form of FIG. 3, the flowcell, indicated generally at 46, has a tubular wall structure which is not straight, unlike the tubular wall structure 36, but is curvilinear. The wall structure may be U shaped, for example, but in the illustrated form is of helical form and indicated at 48. In this manner, the fluid and sight path, indicated at 50, may be elongated for liquid flowed therethrough to give greater sensitivity as in colorimetric measurements of the constituent of interest in the sample. As indicated, the optical axis 52 is the axis of the tubular wall structure 48 and conforms to the helix of the path 50. The tubular wall structure 48 may be structured of cadmium having a refractive index of 1.13. By way of example, and not by limitation, the sight path of the flowcell 46 which includes the path 50 and portions of the ducts of the nipples 54, 56 may be 100mm long, for example. Also, the diameter of the path 50 may be 1.0mm and the outer diameter of the wall structure 48 may be 2.0mm. One advantage of a tubular wall structure of a flowcell which is U shaped or is of helical form as shown, is that the sight path 50 may be long as indicated, while permitting the flowcell to be fitted into a small space.

As indicated in the last-mentioned view, the flow inlet and outlet nipples 54 and 56, respectively, which may be cylindrical, may be structured of glass, for example, and each have a portion which is sealed in the respective ends of the tubular wall structure 48 in flush relation to the flow path 50 of such wall structure. Each of the nipples 54, 56 is bent, both internally and externally, at a right angle as shown to change the direction of fluid flow for the optical axis to extend through the side of such nipple, an end window, in the manner indicated.

It is to be understood that the light source and photodetector may be disposed at opposite ends of the flowcell in alignment with the optical input and output thereof. However, if desired, as in the form of FIG. 1, fiber optics may be utilized for light transmission intermediate the light source and one end window and intermediate the other end window in the photodetector, so that the light source and the photodetector are not required to be in such alignment.

In the operation of the form of FIG. 1 of the invention by way of example, the sample stream in the tube 16 may be segmented with immiscible fluid segments and comprise a series of blood serum samples flowing successively therein. The samples are diluted at a 6:1 ratio with water. The constituent of interest in each sample analyzed quantitatively may be cholesterol. The diluted sample, having an index of refraction of 1.34 or close thereto is flowed in tube 16 at a rate of 0.08ml/min. or close thereto. Lieberman-Burchard reagent is flowed in tube 12 at a rate of 0.96ml/min. or close thereto. This reagent is essentially 60% acetic anhydride, 30% acetic acid and 10% sulfuric acid. The reagent has an index of refraction of 1.40. When diluted serum samples are proportioned with the Leiberman-Burchard reagent in the tube 12, the resultant mixture has a refractive index of 1.39, higher than the previously indicated index of refraction of 1.338 of the material of the tubular wall structure 36 of the flowcell with which such mixture interfaces as it flows through the flow path of the flowcell.

As a result, the last-mentioned mixture flowing through the last-mentioned wall structure functions as a light pipe with a significant improvement in light transmission through the flowcell. In fact, distinguishing conventional prior art combinations, essentially 100% of the light entering the flow path through the tubular wall structure is utilized therein by reflectivity at the interface of the last-mentioned mixture with the wall structure 36, and essentially none of the light is refracted into the wall structure 36. There is a significant improvement in light transmission through the flowcell by light piping, even in applications where some of the light entering the fluid path of the tubular wall structure 36 is refracted in the wall structure, and the utilization of such light is not 100%. In accordance with the invention, there is also a significant improvement in analysis by a substantial reduction of optical artifacts. The quantitative analysis of the constituent of interest in the described form of FIG. 1 is by light absorbance or transmission. The stream exits from the flowcell through the nipple 24 and is conducted to waste by the tube 22.

In the operation of the form of FIG. 3 of the invention by way of example, the sample may be a pharmaceutical preparation and the constituent of interest may be chlorpheniramine maleate in the range of 0–4mg% the sample may be treated in a conventional manner for colorimetric analysis in a flowcell. The liquid stream, discounting any wash solution segments, flowing into the inlet nipple 54 of the flowcell 46 and out the outlet nipple 56 is essentially chloroform having an index of refraction of 1.444, and such liquid stream may be segmented with immiscible fluid segments such as gas. Specifically, such liquid stream may consist of a mixture of ethyl orange-chloropheniramine maleate ion pair complex and chloroform, wherein the proportions are approximately 2mg ethyl orange to 2ml. chloroform. This mixture has a refractive index of 1.44 or close thereto, which is higher than the cadmium of the tubular wall structure 48. The mixture constitutes a light pipe for light transmission therethrough by reflectivity at the interface of the mixture with the cadmium of the wall structure 48.

It is to be understood that the end caps 38 of the form of FIG. 1 may be formed as an integral part of the body 36 of the flowcell, provided that the material from which the body or tubular wall structure 36 is structured, has sufficient light transmission characteristics.

While plural forms of the invention have been illustrated and described, it will be understood, especially by those versed in the art, that the invention may take other forms, and that the invention is susceptible of various changes in details without departure from the principles thereof.

What is claimed is:

1. A photometric system comprising: a source of different blood samples treated with a same reagent, means for flowing said samples successively along a conduit from said source in isolated condition from another, a flow cell in said conduit having a tubular wall structure formed at least internally with a portion defining a straight sight path through which said samples flow, a light source, means directing a ray from said light source so as to pass said ray through said sight path for detection of said ray, and photodetection means successively measuring at a particular wavelength the light absorbance of said samples in said sight path, said samples having a first index of refraction, said flow cell portion having a second index of refraction which is less than said first index of refraction.

2. Apparatus as defined in claim 1, further including means on the flowcell defining end windows at the respective ends of said wall structure.

3. Apparatus as defined in claim 1, wherein: said flowcell comprises windowed end caps at the respective ends of said wall structure, said end caps defining a fluid inlet and a fluid outlet respectively.

4. Apparatus as defined in claim 1, wherein: said portion of the said tubular wall structure which interfaces with said liquid is constituted by fluoronated ethylene-propylene resin.

5. Apparatus as defined in claim 1, wherein: said portion of said tubular wall structure which interfaces with said liquid is cadmium.

6. Apparatus as defined in claim 2, wherein: said means on the flowcell defining the end window which is a light output window comprises a fluid outlet portion of the flowcell, said outlet portion in the area of the light-named window being formed in part on a radius.

7. Apparatus as defined in claim 1, wherein a constituent of interest in the samples is cholesterol and said samples are different specimens of blood serum, said reagent is Lieberman-Burchard reagent, and said portion of said tubular wall structure interfacing with said treated samples is constituted by fluoronated ethylene-propylene resin.

* * * * *